United States Patent [19]

Stetter et al.

[11] 4,117,154
[45] Sep. 26, 1978

[54] PESTICIDALLY ACTIVE NOVEL OXIME-CARBAMATES OF FLUORINATED KETONES

[75] Inventors: Jörg Stetter, Wuppertal; Ingeborg Hammann, Cologne; Bernhard Homeyer, Leverkusen; Wolfgang Behrenz, Overath, all of Germany

[73] Assignee: Bayer Aktiengesellschaft, Leverkusen, Germany

[21] Appl. No.: 815,045

[22] Filed: Jul. 12, 1977

[30] Foreign Application Priority Data

Jul. 14, 1976 [DE] Fed. Rep. of Germany ....... 2631522

[51] Int. Cl.$^2$ .................. A01N 9/12; C07C 131/11; C07C 121/38; C07C 121/60
[52] U.S. Cl. ..................... 424/298; 260/453 RW; 260/566 AC; 424/327; 260/465.4; 260/465 D; 560/251; 560/147; 560/168; 560/9; 560/22
[58] Field of Search ............... 260/453 RW, 566 AC, 260/465.4, 465 D; 424/298, 327; 560/251, 147, 168, 9, 22

[56] References Cited

U.S. PATENT DOCUMENTS 4,029,688  6/1977  D'Silva ..................... 260/453 RW

*Primary Examiner*—Lewis Gotts
*Assistant Examiner*—Robert C. Whittenbaugh
*Attorney, Agent, or Firm*—Burgess, Dinklage & Sprung

[57] ABSTRACT

Oxime-carbamates of fluorinated ketones of the formula $$R-C(\!\!\begin{array}{c}N-O-CO-N\diagdown^{R^1}_{R^2}\\CHFX\end{array}\!\!) \quad (I)$$

in which

X represents hydrogen or fluorine,

R represents alkyl, cycloalkyl, phenyl or phenylalkyl, any of which can optionally be substituted, $R^1$ and $R^2$, which may be identical or different, each represent hydrogen, alkyl, alkenyl, alkynyl, halogenoalkyl, halogenoalkenyl, alkoxyalkyl, alkylthioalkyl or optionally substituted phenyl, and $R^2$ can also represent the $-SR^3$ grouping, $R^3$ represents alkyl, halogenoalkyl, optionally substituted phenyl or alkoxycarbonyl, or represents a radical identical to that to which the $-SR^3$ grouping is bonded, or represents the $$-\underset{\underset{R^4}{|}}{N}-SO_2-R^5$$

grouping, wherein $R^4$ represents alkyl and $R^5$ represents alkyl, dialkylamino or optionally substituted phenyl, and acid addition salts thereof, which possess insecticidal, acaricidal, nematicidal and fungicidal properties.

9 Claims, No Drawings

PESTICIDALLY ACTIVE NOVEL OXIME-CARBAMATES OF FLUORINATED KETONES

The present invention relates to and has for its objects the provision of particular new oxime-carbamates of fluorinated ketones which possess insecticidal, acaricidal and nematicidal properties, active compositions in the form of mixtures of such compounds with solid and liquid dispersible carrier vehicles, and methods for producing such compounds and for using such compounds in a new way especially for combating pests, e.g. insects, acarids and nematodes, with other and further objects becoming apparent from a study of the within specification and accompanying examples.

It has already been disclosed that certain oxime-carbamates of chlorinated ketones, such as, for example, 1-chloro-3,3-dimethyl-2-methylcarbamoyloximino-butane, possess pesticidal properties (see German Offenlegungsschrift (German Published Specification) 2,216,838). Their action is, however, not always entirely satisfactory, especially if low concentrations are used.

The present invention now provides, as new compounds, the oxime-carbamates of fluorinated ketones, of the general formula

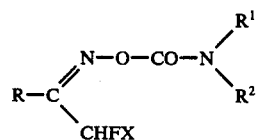 (I)

in which

X represents hydrogen or fluorine,

R represents alkyl, cycloalkyl, phenyl or phenylalkyl, any of which can optionally be substituted, $R^1$ and $R^2$, which may be identical or different, each represent hydrogen, alkyl, alkenyl, alkynyl, halogenoalkyl, halogenoalkenyl, alkoxyalkyl, alkylthioalkyl or optionally substituted phenyl, and $R^2$ can also represent the —$SR^3$ grouping, wherein $R^3$ represents alkyl, halogenoalkyl optionally substituted phenyl or alkoxycarbonyl, or represents a radical identical to that to which the —$SR^3$ grouping is bonded, or represents the

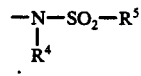

grouping, wherein $R^4$ represents alkyl and $R^5$ represents alkyl, dialkylamino or optionally substituted phenyl, and also their acid-addition salts.

Preferably, R represents straight-chain or branched alkyl with 1 to 6 carbon atoms, which can optionally be substituted by halogen (especially fluorine, chlorine or bromine), nitro, cyano or hydroxyl or by a grouping —$SR^6$, —$OR^6$, —CO—$OR^6$ or —O—CO—$R^6$, wherein $R^6$ represents alkyl with 1 to 4 carbon atoms, or R represents phenyl which can optionally be substituted by halogen (especially fluorine, chlorine or bromine), alkyl with 1 to 4 carbon atoms or halogenoalkyl with 1 or 2 carbon atoms and up to 5 halogen atoms (preferably fluorine atoms and/or chlorine atoms, trifluoromethyl being an example of such halogenoalkyl), or represents phenylalkyl with 1 to 4 carbon atoms in the alkyl part, which is optionally substituted, in the phenyl part, by halogen (especially fluorine, chlorine or bromine), alkyl with 1 to 4 carbon atoms or halogenoalkyl with 1 or 2 carbon atoms and up to 5 halogen atoms (preferably fluorine atoms and/or chlorine atoms, trifluoromethyl being an example of such halogenoalkyl), or represents cycloalkyl with 5 to 7 carbon atoms which is optionally substituted by halogen (especially fluorine, chlorine or bromine), alkyl with 1 to 4 carbon atoms or halogenoalkyl with 1 or 2 carbon atoms and up to 5 halogen atoms (preferably fluorine atoms and/or chlorine atoms, trifluoromethyl, chlorodifluoromethyl, dichlorofluoromethyl and trichloromethyl being examples of such halogenoalkyl); and $R^1$ and $R^2$, which may be identical or different, each represent hydrogen, straight-chain or branched alkyl with 1 to 12 carbon atoms, alkenyl or alkynyl each with 2 to 4 carbon atoms, halogenoalkyl with up to 2 carbon atoms and up to 5 halogen atoms (preferably fluorine atoms and/or chlorine atoms, trifluoromethyl being an example of such halogenoalkyl), halogenoalkenyl with up to three carbon atoms and up to 5 halogen atoms (preferably fluorine atoms and/or chlorine atoms), alkoxyalkyl or alkylthioalkyl with up to 2 carbon atoms in each alkyl part, or phenyl which is optionally substituted by halogen (especially fluorine, chlorine or bromine), alkyl with 1 to 4 carbon atoms, halogenoalkyl, halogenoalkoxy or halogenoalkylthio each with 1 to 2 carbon atoms and up to 5 halogen atoms (preferably fluorine atoms and/or chlorine atoms, trifluoromethyl, trifluoromethoxy, trifluoromethylthio, chlorodifluoromethyl, chlorodifluoromethoxy and chlorodifluoromethylthio being examples of such radicals), alkoxy or alkylthio each with 1 or 2 carbon atoms, optionally halogen-substituted (especially fluorine- or chlorine-substituted) phenyl or phenoxy, nitro or cyano; or $R^2$ represents the —$SR^3$ grouping, wherein $R^3$ represents alkyl with 1 to 4 carbon atoms, halogenoalkyl with 1 or 2 carbon atoms and up to 5 halogen atoms (preferably fluorine atoms and/or chlorine atoms, trifluoromethyl, chlorodifluoromethyl, dichlorofluoromethyl and trichloromethyl being examples of such halogenoalkyl radicals), phenyl which is optionally substituted by halogen (especially fluorine, chlorine or bromine), alkyl with 1 or 2 carbon atoms or halogenoalkyl with 1 to 2 carbon atoms and up to 5 halogen atoms (preferably fluorine atoms and/or chlorine atoms, the trifluoromethyl group being an example of such halogenoalkyl), or represents alkoxycarbonyl with 1 to 4 carbon atoms in the alkoxy part or a radical identical to that to which the —$SR^3$ grouping is bonded, or $R^3$ represents the —$NR^4$—$SO_2$—$R^5$ radical, wherein $R^4$ represents alkyl with 1 to 4 carbon atoms and $R^5$ represents alkyl with 1 to 5 carbon atoms, dialkylamino with 1 to 4 carbon atoms in each alkyl part, or phenyl which is optionally substituted by halogen (especially fluorine, chlorine or bromine), alkyl with 1 or 2 carbon atoms, halogenoalkyl with 1 or 2 carbon atoms and up to 5 halogen atoms (preferably fluorine atoms and/or chlorine atoms, trifluoromethyl being an example of such halogenoalkyl), cyano or nitro.

Surprisingly, the oxime-carbamates of fluorinated ketones, according to the invention, possess a better insecticidal, soil-insecticidal, acaricidal nematicidal action than the previously known oxime-carbamates of chlorinated ketones, such as, for example, 1-chloro-3,3-dimethyl-2-methylcarbamoyl-oximino-butane, which, chemically and in respect of their action, represent the closest compounds. The new products are not only active against leaf insects and soil insects, mites and nematodes, but also against pests harmful to health and pests of stored products. Accordingly, they represent a genuine enrichment of the art.

The present invention also provides a process for the preparation of an oxime-carbamate of a fluorinated ketone, of the formula (I), in which (a) an oxime of a fluorinated ketone, of the general formula

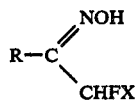  (II)

in which
R and X have the abovementioned meanings,
(1) is reacted with an isocyanate of the general formula $R^1 - N = C = O$  (III), in which
$R^1$ has the abovementioned meaning,
if appropriate in the presence of a diluent and/or of a catalyst, or
(2) is reacted with a carbamoyl halide of the general formula

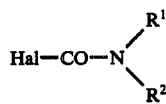  (IV), in which
$R^1$ and $R^2$ have the abovementioned meanings and
Hal represents fluorine or chlorine,
if appropriate in the presence of a diluent and/or of an acid-binding agent, or
(3), in the case where $R^1$ and $R^2$ denote hydrogen, is reacted with an alkali metal cyanate of the general formula

M — OCN  (V), in which
M represents sodium, potassium or ammonium, if appropriate in the presence of hydrochloric acid and of a diluent, or (b), when $R^2$ represents the $-SR^3$ grouping, an oxime-carbamate, obtainable according to process variant (a), of the general formula

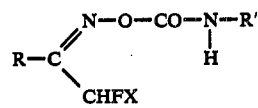  (VI), in which
R, $R^1$ and X have the abovementioned meanings, is reacted with a sulphene chloride of the general formula Cl — S — $R^3$  (VII), in which
$R^3$ has the abovementioned meaning,
if appropriate in the presence of a diluent and of an acid-binding agent.

If 1,1-difluoro-3,3-dimethyl-2-oximino-butane and methyl isocyanate are used as starting materials in process variant (a) (1), the course of the reaction can be represented by the following equation:

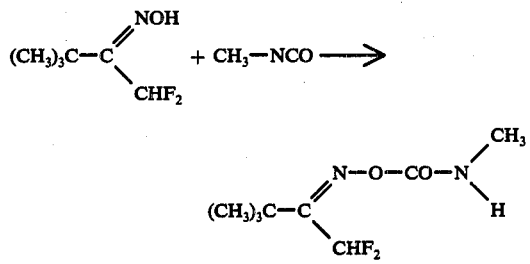

If 1-fluoro-3-methyl-2-oximino-butane and N,N'-bis-(fluorocarbonyl)-thio-bis-methylamine are used as starting materials in process variant (a) (2), the course of the reaction can be represented by the following equation:

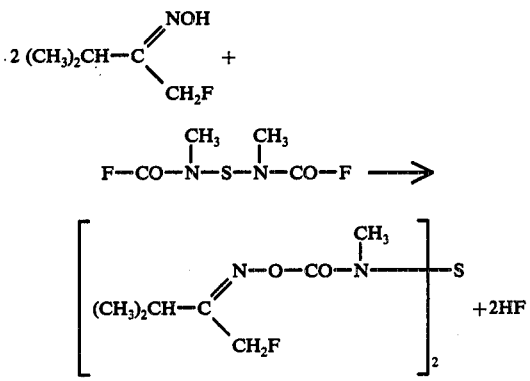

If 1,1-difluoro-3,3-dimethyl-2-oximino-butane and sodium cyanate in hydrochloric acid are used as the starting materials in process variant (a) (3), the course of the reaction can be represented by the following equation:

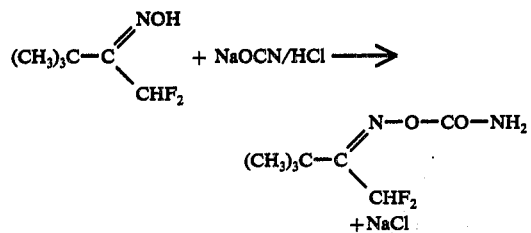

If 1,1-difluoro-3,3-dimethyl-2-methylcarbamoyloximino-butane and methoxycarbonylsulphene chloride are used as starting materials in process variant (b), the course of the reaction can be represented by the following equation:

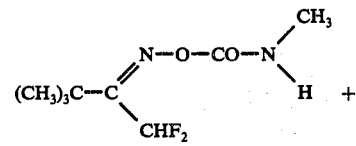

-continued

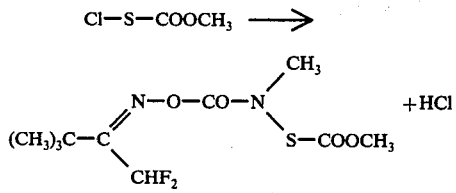 +HCl

The following may be mentioned as examples of starting materials of the formula (II): 1-fluoro-3,3-dimethyl-2-oximino-butane, 1-fluoro-2-oximino-butane, 1-fluoro-2-oximino-propane, 1-fluoro-3-methyl-2-oximino-butane, 1-fluoro-2-oximino-2-phenyl-ethane, 2-(4-chlorophenyl)-1-fluoro-2-oximino-ethane, 2-(2,4-dichlorophenyl)-1-fluoro-2-oximino-ethane, 1-fluoro-2-oximino-3-phenyl-propane, 3-(2,4-dichlorophenyl)-1-fluoro-2-oximino-propane, 1-fluoro-3,3-dimethyl-2-oximino-3-phenyl-propane, 2-cyclopentyl-1-fluoro-2-oximino-ethane, 2-cyclohexyl-1-fluoro-2-oximino-ethane, 2-cycloheptyl-1-fluoro-2-oximino-ethane, 1-fluoro-2-(1-methylcyclohexyl)-2-oximino-ethane, 3,3-dimethyl-1-fluoro-2-oximino-pentane, 3-ethyl-1-fluoro-3-methyl-2-oximino-pentane, 1-fluoro-3-methyl-2-oximino-pentane, 3-ethyl-1-fluoro-2-oximino-pentane, 4-chloro-3,3-dimethyl-1-fluoro-2-oximino-butane, 4-bromo-3,3-dimethyl-1-fluoro-2-oximino-butane, 3,3-dimethyl-1-fluoro-4-hydroxy-2-oximino-butane, 4-acetoxy-3,3-dimethyl-1-fluoro-2-oximino-butane, 1,4-difluoro-3,3-dimethyl-2-oximino-butane, 3,3-dimethyl-1-fluoro-4-methoxy-2-oximino-butane, 3,3-dimethyl-1-fluoro-4-methylthio-2-oximino-butane, 1-fluoro-2-(1-fluoromethylcyclohexyl)-2-oximino-ethane, 2-(1-chloromethyl-cyclohexyl)-1-fluoro-2-oximino-ethane, 3,3-bis-chloromethyl-1-fluoro-2-oximino-butane, 3,3-bis-fluoromethyl-1-fluoro-2-oximino-butane, 3,3-bis-fluoromethyl-1-fluoro-2-oximino-pentane, 3,3-dimethyl-1-fluoro-4-nitro-2-oximino-butane, 4-cyano-3,3-dimethyl-1-fluoro-2-oximino-butane, 5-cyano-3,3-dimethyl-1-fluoro-2-oximino-pentane, 2,2-dimethyl-4-fluoro-3-oximinobutyric acid ethyl ester, 3-cyano-1-fluoro-3-methyl-2-oximino-butane, 1-fluoro-3-methyl-3-nitro-2-oximino-butane, 1,3-difluoro-3-methyl-2-oximino-butane, 1,1-difluoro-3,3-dimethyl-2-oximino-butane, 1,1-difluoro-2-oximino-butane, 1,1-difluoro-2-oximino-propane, 1,1-difluoro-3-methyl-2-oximino-butane, 1,1-difluoro-2-oximino-2-phenyl-ethane, 2-(4-chlorophenyl)-1,1-difluoro-2-oximino-ethane, 2-(2,4-dichloro-phenyl)-1,1-difluoro-2-oximino-ethane, 1,1-difluoro-2-oximino-3-phenyl-propane, 3-(2,4-dichlorophenyl)-1,1-difluoro-2-oximino-propane, 1,1-difluoro-3,3-dimethyl-2-oximino-3-phenyl-pentane, 2-cyclopentyl-1,1-difluoro-2-oximino-ethane, 2-cyclohexyl-1,1-difluoro-2-oximino-ethane, 2-cycloheptyl-1,1-difluoro-2-oximino-ethane, 1,1-difluoro-2-(1-methylcyclohexyl)-2-oximino-ethane, 1,1-difluoro-3,3-dimethyl-2-oximino-pentane, 3-ethyl-1,1-difluoro-3-methyl-2-oximino-pentane, 1,1-difluoro-3-methyl-2-oximino-pentane, 3-ethyl-1,1-difluoro-2-oximino-pentane, 4-chloro-1,1-difluoro-3,3-dimethyl-2-oximino-butane, 4-bromo-1,1-difluoro-3,3-dimethyl-2-oximino-butane, 1,1-difluoro-3,3-dimethyl-4-hydroxy-2-oximino-butane, 4-acetoxy-1,1-difluoro-3,3-dimethyl-2-oximino-butane, 1,1-difluoro-3,3-dimethyl-4-methoxy-2-oximino-butane, 1,1-difluoro-3,3-dimethyl-4-methylthio-2-oximino-butane, 1,1-difluoro-2-(1-fluoromethylcyclohexyl)-2-oximino-ethane, 2-(1-chloromethyl-cyclohexyl)-1,1-difluoro-2-oximino-ethane, 3,3-bis-chloromethyl-1,1-difluoro-2-oximino-butane, 3,3-bis-fluoromethyl-1,1-difluoro-2-oximino-butane, 3,3-bis-fluoromethyl-1,1-difluoro-2-oximino-pentane, 1,1-difluoro-3,3-dimethyl-4-nitro-2-oximino-butane, 4-cyano-1,1-difluoro-3,3-dimethyl-2-oximino-butane, 5-cyano-1,1-difluoro-3,3-dimethyl-2-oximino-pentane, 4,4-difluoro-2,2-dimethyl-3-oximino-butyric acid ethyl ester, 3-cyano-1,1-difluoro-3-methyl-2-oximino-butane, 1,1-difluoro-3-methyl-3-nitro-2-oximino-butane, 3-methyl-1,1,3-trifluoro-2-oximino-butane and 3,3-dimethyl-1,1,4-trifluoro-2-oximino-butane.

The oximes of fluorinated ketones of the formula (II) have not previously been described in the literature. However, they can be prepared in a simple manner by reacting fluorinated ketones of the general formula

in which
R and X have the abovementioned meanings, with hydroxylamine in the presence of a solvent, preferably an alcohol or aqueous alcohol, at temperatures between 20° and 100° C, preferably between 50° and 80° C. In this reaction, the hydroxylamine is preferably employed in the form of a salt, especially as the hydrochloride, in the presence of an acid-binding agent such as, for example, sodium carbonate. The compounds of the formula (II) are isolated by working up the product, formed during the reaction, in accordance with customary methods after distilling off the solvent, as shown in the preparative examples hereinbelow.

Fluorinated ketones of the formula (VIII) are disclosed in U.S. Pat. No. 3,520,942 and can easily be prepared in accordance with the processes there described by reacting the corresponding brominated or chlorinated ketones with potassium fluoride at high temperatures, also shown hereinbelow.

The following may be mentioned as examples of starting materials of the formula (III): methyl isocyanate, ethyl isocyanate, i-propyl isocyanate, t-butyl isocyanate, heptyl isocyanate, dodecyl isocyanate, allyl isocyanate, propargyl isocyanate, trifluoromethyl isocyanate, chloromethyl isocyanate, chloroethyl isocyanate, trichlorovinyl isocyanate, methoxymethyl isocyanate, ethoxymethyl isocyanate, methoxyethyl isocyanate, phenyl isocyanate, 4-chlorophenyl isocyanate, 2,4-dichloro-phenyl isocyanate, 3-chloro-4-methylphenyl isocyanate, 3-trifluoromethylphenyl isocyanate, 4-ethoxyphenyl isocyanate, 4-nitrophenyl isocyanate, 3-chloro-4-dichlorofluoromethylphenyl isocyanate and 4-(4'-chlorophenoxy)-phenyl isocyanate.

The isocyanates of the formula (III) are known or can be prepared in accordance with generally customary and known processes, for example by reacting amines with phosgene and subsequent heating. These processes are known from the general textbooks of organic chemistry.

Examples of starting materials of the formula (IV) which may be mentioned are: methylcarbamoyl chloride, dimethylcarbamoyl chloride, methylethylcarbamoyl chloride, allylmethylcarbamoyl chloride, methoxymethyl-methylcarbamoyl chloride, methyl-trifluoromethylcarbamoyl chloride, ethylvinylcarbamoyl chloride, N-fluorodichloromethylsulphenyl-N-phenyl-carbamic acid fluoride, N,N'-bis-(fluorocarbonyl)-thiobis-methylamine, N-methyl-N-trichloromethylsulphenyl-carbamic acid fluoride, N-methyl-N-fluorodichloromethylsulphenyl-carbamic acid fluoride, N-methyl-N-chlorodifluoromethylsulphenyl-carbamic acid fluoride, N-methyl-N-(3-trifluoromethylphenyl)-sulphenylcarbamic acid fluoride, N-methyl-N-(methoxycarbonylsulphenyl)-carbamic acid fluoride and N-methyl-N-[(3-methylphenyl-sulphonyl)-methylaminosulphenyl]-carbamic acid fluoride.

The carbamoyl halides of the formula (IV) are known and can be prepared in accordance with generally customary and known processes. Thus, for example, the carbamoyl chlorides are obtained by reacting amines with phosgene as shown in general textbooks of organic chemistry. The sulphenylated carbamoyl fluorides are obtained, for example, by reacting the corresponding carbamic acid fluorides with the corresponding sulphene chlorides (see German Auslegeschrift (German Published Specification) No. 1,297,095, U.S. Pat. No. 3,939,192 and German Offenlegungsschriften (German Published Specifications) Nos. 2,357,930 and 2,409,463).

Examples of starting materials of the formula (VII) which may be mentioned are: trichloromethylsulphene chloride, dichlorofluoromethylsulphene chloride, chlorodifluoromethylsulphene chloride, trifluoromethylsulphene chloride, phenylsulphene chloride, 2,4-dichlorophenylsulphene chloride, 3-trifluoromethylphenylsulphene chloride, 3-methylphenylsulphene chloride, methylsulphenyl chloride, 4-chloro-3-trifluoro-methylphenylsulphenyl chloride, methoxycarbonylsulphenyl chloride and ethoxycarbonylsulphenyl chloride.

Possible salts of the compounds of the formula (I) are salts with physiologically tolerated acids. These preferentially include the hydrogen halide acids, such as, for example, hydrobromic acid and, especially, hydrochloric acid, phosphoric acid, nitric acid, monofunctional and bifunctional carboxylic acids and hydroxycarboxylic acids, such as, for example, acetic acid, maleic acid, succinic acid, fumaric acid, tartaric acid, citric acid, salicyclic acid, sorbic acid and lactic acid, and 1,5-naphthalenedisulphonic acid.

The salts of the compounds of the formula (I) can be obtained in a simple manner by the customary methods of forming salts, for example by dissolving the base in ether, for example diethyl ether, and adding the acid, for example phosphoric acid, and can be isolated in the known manner, for example by filtering off, and be purified if appropriate.

Preferred possible diluents for the reaction according to process variant (a) (1) are all inert organic solvents, especially ketones, such as diethyl ketone and especially acetone and methyl ethyl ketone; nitriles, such as propionitrile and especially acetonitrile; alcohols, such as ethanol or isopropanol; ethers, such as tetrahydrofuran or dioxane; formamides, such as, in particular, dimethylformamide; and halogenated hydrocarbons, such as methylene chloride, carbon tetrachloride or chloroform.

Catalysts which can be used preferentially in process variant (a) (1) are tertiary bases, such as triethylamine and pyridine, and organo-tin compounds such as dibutyl-tin dilaurate (Desmorapid).

The reaction temperatures can be varied within a fairly wide range when carrying out process variant (a) (1). In general the reaction is carried out at from 0° to 100° C, preferably at from 20° to 85° C.

In carrying out process (a) (1), 1 to 2 moles of isocyanate of the formula (III) are preferably employed per mole of the compound of the formula (II). To isolate the compounds of the formula (I), the solvent is distilled off and the residue is worked up in accordance with customary methods.

Possible diluents for carrying out the reaction according to process variant (a) (2) are all inert organic solvents, especially the solvents recited in connection with process variant (a) (1).

If the reaction according to process variant (a) (2) is carried out in the presence of an acid-binding agent, any of the inorganic and organic acid-binders which can usually be employed may be added. Preferred are the alkali metal carbonates, such as, for example, sodium carbonate, potassium carbonate and sodium bicarbonate, and also lower tertiary alkylamines, cycloalkylamines or aralkylamines, such as, for example, triethylamine, N,N-dimethyl-benzylamine and dicyclohexylmethylamine, as well as pyridine and diazabicyclooctane.

The reaction temperatures of process variant (a) (2) can be varied within a fairly wide range. In general, the reaction is carried out from 0° to 100° C, preferably from 0° to 85° C.

In carrying out process (a) (2), it is preferred to use, per mole of the compound of the formula (II), 1 to 2 moles, or in the case of a dimeric product 0.5 mole, of carbamoyl chloride of the formula (IV), and 1 to 2 moles of acid-binding agent. The compounds of the formula (I) are isolated in the generally customary and known manner.

Possible diluents for the reaction according to process variant (a) (3) are inert organic solvents or their mixtures with water. The preferred inert solvents include the solvents recited above in connection with process variant (a) (1).

In carrying out process (a) (3), the reaction temperatures can be varied within a fairly wide range. In general, the reaction is carried out at from 0° to 50° C, preferably from 0° to 30° C.

In carrying out process (a) (3), preferably 1 to 2 moles of the alkali metal cyanate, preferably sodium cyanate, are employed per mole of the compound of the formula (II). To isolate the compounds, the organic phase is separated off, the solvent is distilled off and the residue is worked up in accordance with customary methods.

Possible diluents for the reaction according to process variant (b) are inert organic solvents, especially the solvents recited in connection with process variant (a) (1).

The reaction according to process variant (b) is carried out in the presence of an acid-binding agent, any of the inorganic and organic acid-binders which can usually be employed may be added. The preferred acid-binders include the acid-binding agents recited above in connection with process variant (a) (2).

In carrying out process variant (b), the reaction temperatures can be varied within a fairly wide range. In general, the reaction is carried out at from 0° to 100° C, preferably from 20° to 50° C.

In carrying out process variant (b), the starting compounds are preferably employed in equimolar amounts. The compounds of the formula (I) are isolated in accordance with customary methods.

In addition to those of the preparative examples hereinbelow, the following are particularly active representative compounds according to the invention: 1,1- difluoro-3-methyl-2-methylcarbamoyl-oximino-butane, 1,1-difluoro-3-methyl-2-(N-methyl-N-trichloromethyl-mercapto)-carbamoyloximino-butane, 1,1-difluoro-3-methyl-2-(N-methyl-N-trichlorofluoromethylmercapto)-carbamoyl-oximino-butane, 1,1-difluoro-3-methyl-2-[N-methyl-N-(3-trifluoromethylphenylmercapto)]-carbamoyloximino-butane, 1,1-difluoro-3-methyl-2-[N-methyl-N-(4-chlorophenylmercapto)]-carbamoyloximino-butane, 1,1-difluoro-3-methyl-2-[N-methyl-N-(4-methylphenylsulphonyl)-methylaminomercapto]-carbamoyloximino-butane, 1,1-difluoro-3-methyl-2-[N-methyl-N-(dimethylaminosulphonyl)-methyl-aminomercapto]-carbamoyloximino-butane, 2-cyclohexyl-1,1-difluoro-2-[N-methyl-N-(dimethylaminosulphonyl)-methyl-aminomercapto]-carbamoyloximino-ethane, 2-cyclohexyl-1-fluoro-2-N-methyl-N-(dimethylaminosulphonyl)-methyl-aminomercapto-carbamoyloximino-ethane, 1,1-difluoro-2-(1-methyl-cyclohexyl)-2-[N-methyl-N-(dimethylaminosulphonyl)-methyl-aminomercapto]-carbamoyloximino-ethane, 1-fluoro-2-(1-methylcyclohexyl)-2-[N-methyl-N-(dimethylaminosulphonyl)-methylaminomercapto]-carbamoyloximino-ethane, 4-chloro-1,1-difluoro-3,3-dimethyl-2-methylcarbamoyloximino-butane, 4-chloro-1-fluoro-3,3-dimethyl-2-methylcarbamoyloximino-butane, 1,4-difluoro-3,3-dimethyl-2-methylcarbamoyloximino-butane, 1,1,4-trifluoro-3,3-dimethyl-2-methylcarbamoyloximino-butane, 1-fluoro-4-nitro-3,3-dimethyl-2-methylcarbamoyloximino-butane, 1,1-difluoro-4-nitro-3,3-dimethyl-2-methylcarbamoyloximino-butane, 4-cyano-1-fluoro-3,3-dimethyl-2-methylcarbamoyloximino-butane, 4-cyano-1,1-difluoro-3,3-dimethyl-2-methylcarbamoyloximino-butane, 4-acetoxy-1-fluoro-3,3-dimethyl-2-methylcarbamoyloximino-butane, 4-acetoxy-1,1-difluoro-3,3-dimethyl-2-methylcarbamoyloximino-butane, 4-ethylcarbonyloxy-1-fluoro-3,3-dimethyl-2-methylcarbamoyloximino-butane, 4-ethylcarbonyloxy-1,1-difluoro-3,3-dimethyl-2-methylcarbamoyloximino-butane, 3-ethoxycarbonyl-1-fluoro-3-methyl-2-methylcarbamoyloximino-butane, 3-ethoxycarbonyl-1,1-difluoro-3-methyl-2-methylcarbamoyloximino-butane, 3,3- dimethyl-1-fluoro-4-methylmercapto-2-methylcarbamoyloximino-butane, 1,1-difluoro-3,3-dimethyl-4-methylmercapto-2-methylcarbamoyloximino-butane, 1-fluoro-3-methyl-3-methylmercapto-2-methylcarbamoyloximino-butane, 1,1-difluoro-3-methyl-3-methylmercapto-2-methylcarbamoyloximino-butane, 1-fluoro-3-methyl-3-nitro-2-methylcarbamoyloximino-butane, 1,1-difluoro-3-methyl-3-nitro-2-methylcarbamoyloximino-butane, 1,3-difluoro-3-methyl-2-methylcarbamoyloximino-butane, 1,1,3-trifluoro-3-methyl-2-methylcarbamoyloximino-butane, and N,N'-bis-(1,1-difluoro-2-oximinocarbonyl-3-methylbutane)-thio-bis-methylamine.

The active compounds are well tolerated by plants, have a favorable level of toxicity to warm-blooded animals, and can be used for combating arthropod pests, especially insects and arachnids, and nematodes which are encountered in agriculture, in forestry, in the protection of stored products and of materials, and in the hygiene field. They are active against normally sensitive and resistance species and against all or some stages of development. The abovementioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and *Scutigera spec.;* from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus, Gryllotalpa spp., Locusta migratoria migratorioides, Melanoplus differentialis* and *Schistocerca gregaria;* from the order of the Dermaptera for example *Forficula auricularia;* from the order of the Isoptera, for example *Reticulitermes spp.;* from the order of the Anoplura, for example *Phylloxera vastatrix, Pemphigus spp., Pediculus humanus corporis, Haematopinus spp.* and *Linognathus spp.;* from the order of the Mallophaga, for example *Trichodectes spp.* and *Damalinea spp.;* from the order of the Thysanoptera, for example *Hercinothrips femoralis* and *Thrips tabaci;* from the order of the Heteroptera, for example *Eurygaster spp., Dysdercus intermedius, Piesma quadrata, Cimex lectularius, Rhodnius prolixus* and *Triatoma spp.;* from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae, Myzus spp., Phorodon humuli, Rhopalosiphum padi, Empoasca spp., Euscelis bilobatus, Nephotettix cincticeps, Lecanium corni, Saissetia oleae, Laodelphax striatellus, Nilaparvata lugens Aonidiella aurantii, Aspidiotus hederae, Pseudococcus spp.* and *Psylla spp.;* from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoae, Lymantria spp., Bucculatrix thurberiella, Phyllocnistis citrella, Agrotis spp., Euxoa spp., Feltia spp., Earias insulana, Heliothis spp., Laphygma exigua, Mamestra brassicae, Panolis flammae, Prodenia litura, Spodoptera spp., Trichoplusia ni, Carpocapsa pomonella, Pieris spp., Chilo spp., Pyrausta nubilalis, Ephestia kuehniella, Galleria mellonella, Cacoecia podana, Capua reticulana, Choristoneura fumiferana Clysia ambiguella, Homona magnanima* and *Tortrix viridana;* from the order of the *Coleoptera,* for example *Anobium punctatum, Rhizopertha dominica, Bruchidius obtectus, Acanthoscelides obtectus, Hylotrupes bajulus, Agelastica alni, Leptinotarsa decemlineata, Phaedon, cochleariae, Diabrotica spp., Psylliodes chrysocephala, Epilachna varivestis, Atomaria spp., Oryzaephilus surinamensis, Anthonomus spp., Sitophilus spp., Otiorrhynchus sulcatus, Cosmopolites sordidus, Ceuthorrhynchus assimilis, Hypera postica, Dermestes spp., Trogoderma spp., Anthrenus spp., Attagenus spp., Lyctus spp., Meligethes aeneus, Ptinus spp., Niptus hololeucus, Gibbium psylloides, Tribolium spp., Tenebrio molitor, Agriotes spp., Conoderus spp., Melolontha melolontha, Amphimallon solstitialis* and *Costelytra zealandica;* from the order of the Hymenoptera, for example *Diprion spp., Hoplocampa spp., Lasius spp., Monomorius pharaonis* and *Vespa spp.;* from the order of the Diptera, for example *Aedes spp., Anopheles spp., Culex spp., Drosophila melanogaster, Musca spp., Fannia spp., Calliphora erythrocephala, Lucilia spp., Chrysomyia spp., Cuterebra spp., Gastrophilus spp., Hyppobosca spp., Stomoxys spp., Oestrus spp., Hypoderma spp., Tabanus spp., Tannia spp., Bibio hortulanus, Oxcinella frit, Phorbia spp., Pegomyia hyoscyami, Ceratitis capitata, Dacus oleae* and *Tipula paludosa;* from the order of the Siphonaptera, for example *Xenopsylla cheopis* and *Ceratophyllus spp.;* from the class of the Arachnida, for example *Scorpio maurus* and *Latrodectus mactans;* from the order of the Acarina, for example *Acarus siro, Argas spp., Ornithodoros spp., Dermanyssus gallinae, Eriophyes ribis, Phyllocoptruta oleivora, Boophilus spp., Rhipicephalus spp., Amblyomma spp., Hyalomma spp., Ixodes spp., Psoroptes spp., Chorioptes spp., Sarcoptes spp., Tarsonemus spp., Bryobia praetiosa, Panonychus spp.* and *Tetranychus spp.*

The plant-parasitic nematodes include *Pratylenchus spp., Radopholus similis, Ditylenchus dipasaci, Tylenchulus semipenetrans, Heterodera spp., Meloidogyne spp., Aphelenchoides spp., Longidorus spp., Xiphinema spp.* and *Trichodorus spp.*

In addition, the active compounds according to the invention, used in appropriate concentrations, also show certain fungicidal effects.

When used against hygiene pests and pests of stored products, the active compounds are distinguished by an excellent residual activity on wood and clay as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances and in coating compositions, for use on seed, and formulations used with burning equipment, such as fumigating cartridges, fumigating cans, fumigating coils and the like, as well as ULV cold mist and warm mist formulations.

These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as halogenated hydrocarbons as well as butane, propane, nitrogen and carbon dioxide; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, dichlorodifluoromethane, trichlorofluoromethane, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as solid carriers, ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules; crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other arthropodicides, e.g. insecticides and acaricides, nematicides and fungicides, or bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0000001–100, preferably 0.01–10%, by weight of the mixture. Thus, the present invention contemplates overall compositions which comprise mixtures of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20-100% by weight of the active compound.

When used against nematodes, the preparations are generally applied to an area of agriculture in amounts of 1 to 100 kg of active compound per hectare, and are then incorporated into the soil.

Furthermore, the present invention contemplates methods of selectively killing, combating or controlling pests, e.g. insects, acarids, nematodes and fungi, which comprises applying to at least one of correspondingly (a) such insects, (b) such acarids, (c) such nematodes, (d) such fungi, and (e) the corresponding habitat thereof, i.e. the locus to be protected, e.g. to a growing crop, to an area where a crop is to be grown or to a domestic animal, a correspondingly combative or toxic amount, i.e. an insecticidally, acaricidally, nematocidally or fungicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, and the like.

It will be realized, of course, that the concentration of the particular active compound utilized in admixture with the carrier vehicle will depend upon the intended application. Therefore, in special cases it is possible to go above or below the aforementioned concentration ranges.

The insecticidal, acaricidal and nematicidal activity of the compounds of this invention is illustrated in the following biological examples. In these examples the active compounds according to the present invention are each identified by the same number, given in brackets, as in preparative examples 8 to 11 hereinbelow.

The known comparison compound is identified as follows:

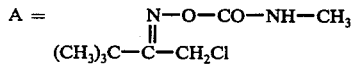

EXAMPLE 1

Plutella test

Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (Brassica oleracea) were sprayed with the preparation of the active compound until dew moist and were then infested with caterpillars of the diamondback moth (Plutella maculipennis).

After the specified periods of time, the degree of destruction was determined as a percentage: 100% meant that all the caterpillars were killed whereas 0% meant that none of the caterpillars were killed.

The active compounds, the concentrations of the active compounds, the evaluation times and the results can be seen from the following table:

Table 1

| Active compounds | (insects which damage plants) Plutella test | |
|---|---|---|
| | Active compound concentration in % | Degree of destruction in % after 3 days |
| (A) | 0.1 | 0 |
| (23) | 0.1 | 100 |
| (13) | 0.1 | 100 |
| (1) | 0.1 | 100 |
| )21) | 0.1 | 100 |
| (7) | 0.1 | 100 |
| (19) | 0.1 | 100 |
| (4) | 0.1 | 100 |
| (22) | 0.1 | 100 |
| (2) | 0.1 | 100 |
| (3) | 0.1 | 100 |

EXAMPLE 2

Tetranychus test (resistant)

Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Bean plants (Phaseolus vulgaris) which were heavily infested with the spider mite Tetranychus urticae in all stages of development are sprayed with the preparation of the active compound until dripping wet.

After the specified periods of time, the degree of destruction was determined as a percentage: 100% meant that all the spider mites were killed whereas 0% meant that none of the spider mites were killed.

The active compounds, the concentrations of the active compounds, the evaluation times and the results can be seen from the following table:

Table 2

| Active compounds | (mites which damage plants) Tetranychus test | |
|---|---|---|
| | Active compound concentration in % | Degree of destruction in % after 2 days |
| (A) | 0.1 | 0 |
| (21) | 0.1 | 98 |
| (3) | 0.1 | 90 |

EXAMPLE 3

Critical concentration test/root-systemic action

Test insect: Phaedon cochleariae larvae
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was of practically no importance: only the amount by weight of active compound per unit volume of soil, which is given hereinafter in ppm (= mg/liter), was decisive. The treated soil was filled into pots and these were planted with cabbage (Brassica oleracea). The active compound could in this way be absorbed from the soil by the roots of the plants and be transported into the leaves.

In order to demonstrate the root-systemic effect, exclusively the leaves were infested with the abovementioned test animals after 7 days. After a further 2 days, the evaluation was carried out by counting or estimating the dead insects. The root-systemic action of the active compound was derived from the mortality figures. It was 100% if all the test insects had been killed and 0% if just as many test insects survived as in the case of the untreated control.

The active compounds, the amounts used and the results can be seen from the table which follows:

Table 3

| Root-systemic action/*phaedon cochleriae* larvae | |
|---|---|
| Active compound | Degree of destruction in % at an active compound concentration of 20 ppm |
| (A) | 0 |
| (1) | 100 |
| (22) | 100 |

EXAMPLE 4

Critical concentration test/root-systemic action

Test insect: *Myzus persicae*
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was of practically no importance: only the amount by weight of active compound per unit volume of soil, which is given in ppm (= mg/liter), was decisive. The treated soil was filled into pots and these were planted with cabbage (*Brassica oleracea*). The active compound could in this way be absorbed from the soil by the roots of the plants and be transported into the leaves.

In order to demonstrate the root-systemic effect, exclusively the leaves were infested with the abovementioned test insects after 7 days. After a further 2 days, the evaluation was carried out by counting or estimating the dead insects. The root-systemic action of the active compound was derived from the mortality figures. It was 100% if all the test insects had been killed and 0% if just as many test insects survived as in the case of the untreated control.

The active compounds, the amounts used and the results can be seen from the table which follows:

Table 4

| Root systemic action/*Myzus persicae* | |
|---|---|
| Active compound | Degree of destruction in % at an active compound concentration of 5 ppm |
| (A) | 0 |
| (2) | 100 |
| (23) | 100 |

EXAMPLE 5

Critical concentration test/soil insects

Test insect: *Phorbia antiqua* grubs in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which is quoted in ppm (=mg/l). The soil was filled into pots and the pots were left to stand at room temperature.

After 24 hours the test insects were introduced into the treated soil and after a further 2 to 7 days the degree of effectiveness of the active compound was determined in % by counting the dead and live test insects. The degree of effectiveness was 100% if all test insects had been killed and was 0% if exactly as many test insects were still alive as in the case of the untreated control.

The active compounds, amounts used and results can be seen from the table which follows:

Table 5

| Soil insects/*Phorbia antiqua* grubs in the soil | |
|---|---|
| Active compound | Degree of destruction in % at an active compound concentration of 20 ppm |
| (A) | 0 |
| (21) | 100 |
| (4) | 100 |

EXAMPLE 6

Critical concentration test/nematicides

Test nematode: *Meloidogyne incognita*
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil which was heavily infested with the test nematodes. The concentration of the active compound in the preparation was of practically no importance; only the amount of active compound per unit volume of soil, which is given in ppm (= mg/l), was decisive. The treated soil was filled into pots, lettuce was sown in and the pots were kept at a greenhouse temperature of 27° C.

After 4 weeks, the lettuce roots were examined for infestation with nematodes (root galls), and the degree of effectiveness of the active compound was determined as a percentage. The degree of effectiveness was 100% when infestation was exactly the same as in the case of the control plants in untreated soil which had been infested in the same manner.

The active compound, the amounts applied and the results can be seen from the following table:

| Table 6 | | |
|---|---|---|
| Nematicides (Meloidogyne incognita) | | |
| | Degree of destruction in % at an active compound concentration, in ppm | |
| Active compound (structure) | 20 | 5 |
| (A) | 0 | 0 |
| (4) | 100 | — |
| (23) | — | 100 |

EXAMPLE 7

LT$_{100}$ test

Test insects: Aëdes aegypti
Solvent: Acetone 2 parts by weight of active compound were dissolved in 1,000 parts by volume of solvent. The solution so obtained was diluted with further solvent to the desired concentrations.

2.5 ml of the solution of active compound was pipetted into a Petri dish. On the bottom of the Petri dish there was a filter paper with a diameter of about 9.5 cm. The Petri dish remained uncovered until the solvent had completely evaporated. The amount of active compound per m² of filter paper varied with the concentration of the solution of active compound. About 25 test insects were then placed in the Petri dish and the dish was covered with a glass lid.

The condition of the test insects was checked continuously and the time needed for 100% destruction was determined.

The active compounds, the concentrations of the active compounds, the test insects and the results can be seen from the following table:

Table 7

| LT$_{100}$ test for Diptera (Aedes aegypti) | | |
|---|---|---|
| Active compounds | Active compound concentration of the solution in % | LT$_{100}$ |
| (A) | 0.2 | 3 hrs = 0 |
| (13) | 0.02 | 60' |
| (1) | 0.02 | 60' |
| (7) | 0.02 | 120' |
| (19) | 0.02 | 120' |
| (21) | 0.02 | 60' |
| (4) | 0.02 | 60' |
| (3) | 0.02 | 60' |
| (2) | 0.02 | 180' |
| (23) | 0.02 | 60' |

The process of the present invention is illustrated by the following preparative examples:

EXAMPLE 8

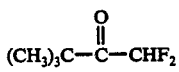

507 g (3 mol) of α,α-dichloropinacoline were slowly added dropwise from a heated dropping funnel, at 180°–190° C. while stirring, to 580 g (10 mol) of dried potassium fluoride in 530 g of ethylene glycol and 200 g of diethylene glycol in a three-neck flask surmounted by a distillation attachment. The α,α-difluoropinacoline thereby produced distilled off continuously. The temperature at the top of the column must not exceed 130° C. After completion of the reaction, the distillate was rectified through a packed column. 300 g (73.5% of theory) of α,α-difluoropinacoline of boiling point 101° C/760 mm Hg were obtained.

PREPARATION OF THE STARTING MATERIAL

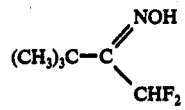

A solution of 53 g of sodium carbonate in 200 ml of water was added dropwise, while stirring, to a mixture of 70 g (0.51 mol) of α,α-difluoropinacoline and 69.5 g (1 mol) of hydroxylamine hydrochloride in 150 ml of ethanol and 100 ml of water. The reaction solution was then stirred for 12 hours at room temperature, after which it was saturated with sodium chloride and extracted by shaking three times with 150 ml of methylene chloride at a time. The combined organic phases were dried over sodium sulphate and concentrated by distilling off the solvent in vacuo. The oily residue was then also distilled. 44.3 g (59% of theory) of 1,1-difluoro-3,3-dimethyl-2-oximino-butane of boiling point of 62°–63° C/9 mm Hg were obtained.

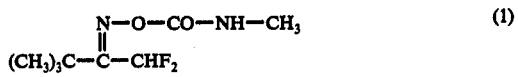

PROCESS VARIANT (a) (1)

75.5 g (0.5 mol) of 1,1-difluoro-3,3-dimethyl-2-oximino-butane and excess methyl isocyanate were heated for 5 hours under reflux in absolute ether. The solvent was then distilled off and the crystalline residue was recrystallized from petroleum ether. 60 g (58% of theory) of 1,1-difluoro-3,3-dimethyl-2-methylcarbamoyloximino-butane of melting point 53°–58° C were obtained.

EXAMPLE 9

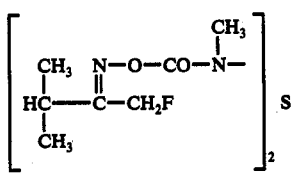

PROCESS VARIANT (a) (2)

5 g (0.042 mol) of 1-fluoro-2-oximino-3-methylbutane and 3.86 g (0.021 mol) of N,N'-bis-(fluorocarbonyl)thio-bis-methylamine were dissolved in 50 ml of absolute dioxane and 4.5 g (0.042 mol) of triethylamine were added slowly at 20°–30° C. After standing for 12 hours at room temperature, the reaction mixture was poured onto 200 ml of water and was repeatedly extracted with methylene chloride. The combined methylene chloride phases were dried over sodium sulphate and concentrated by distilling off the solvent in vacuo. 7 g (87% of theory) of N,N'-bis-(1-fluoro-2-oximinocarbonyl-3-methyl-butane)-thio-bis-methylamine were obtained as a viscous oil.

EXAMPLE 10

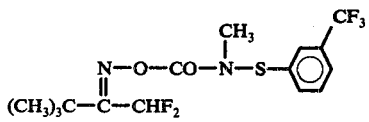 (3)

PROCESS VARIANT (a) (2)

8 g (0.053 mol) of 1,1-difluoro-3,3-dimethyl-2-oximino-butane and 13.4 g (0.053 mol) of N-methyl-N-(m-trifluoromethylphenyl)-sulphenylcarbamic acid fluoride were dissolved in 50 ml of absolute dioxane and 6 g (0.059 mol) of triethylamine were added slowly at 20°–30° C. After standing for 8 hours at room temperature, the reaction mixture was poured onto 200 ml of water and was repeatedly extracted with methyl chloride. The combined methylene chloride phases were dried over sodium sulphate and concentrated by distilling off the solvent in vacuo. The viscous oil which remained crystallized completely after some times. 14 g (68% of theory) of 1,1-difluoro-3,3-dimethyl-2-(N-methyl-N-m-trifluoromethylphenylmercapto)-carbamoyloximino-butane of melting point 46°–53° C were obtained.

EXAMPLE 11

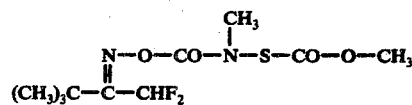 (4)

PROCESS VARIANT (b)

20.8 g (0.1 mol) of 1,1-difluoro-3,3-dimethyl-2-methylcarbamoyloximino-butane (see Example 8) and 10.5 g (0.1 mol) of triethylamine were dissolved in 100 ml of anhydrous toluene. 12.6 g (0.1 mol) of methoxycarbonylsulphenyl chloride were added dropwise while stirring at 20° C (cooling). The mixture was left to stand for 48 hours at room temperature and was filtered. The filtrate was concentrated and the residue was distilled. 15.7 g (53% of theory) of 1,1-difluoro-3,3-dimethyl-2-(N-methyl-N-methoxycarbonylmercapto)-carbamoyl-oximino-butane of melting point 120°–140° C/0.2 mm Hg ($n_D^{20} = 1.4659$) were obtained.

The examples shown below in Table 8 were obtained analogously.

Table 8

$$R-C(\text{CHFX})=N-O-CO-N(R^1)(R^2) \quad (I)$$

| Compound No. | R | R¹ | R² | X | Melting point in ° C, boiling point in ° C/mm Hg or refractive index |
|---|---|---|---|---|---|
| 5 | (CH₃)₃C— | H | 3-CF₃-C₆H₄— | F | viscous oil |
| 6 | (CH₃)₃C— | H | 2-Cl-5-CH₃-C₆H₃— | F | 94–97 |
| 7 | (CH₃)₃C— | H | —CH₂—O—CH₃ | F | 110/22mm |
| 8 | (CH₃)₃C— | H | 4-OC₂H₅-C₆H₄— | F | 128–131 |
| 9 | (CH₃)₃C— | H | 2,4-Cl₂-C₆H₃— | F | 95–98 |
| 10 | (CH₃)₃C— | H | 4-NO₂-C₆H₄— | F | 120–122 |
| 11 | (CH₃)₃C— | H | 4-Cl-C₆H₄— | F | 98–100 |
| 12 | (CH₃)₃C— | H | 3-CF₃-C₆H₄— | H | 99–101 |
| 13 | (CH₃)₃C— | H | CH₃ | H | 58–60 |
| 14 | (CH₃)₃C— | H | 4-(4-Cl-C₆H₄-O)-C₆H₄— | H | 104 |

Table 8-continued $$\begin{array}{c} R^1 \\ N-O-CO-N \\ R-C \\ \diagdown \\ CHFX \end{array} \quad (I) \quad \begin{array}{c} \\ R^2 \end{array}$$

| Compound No. | R | R¹ | R² | X | Melting point in °C, boiling point in °C/mm Hg or refractive index |
|---|---|---|---|---|---|
| 15 | $(CH_3)_3C-$ | H | —⟨phenyl⟩—$OC_2H_5$ | H | 117-120 |
| 16 | $(CH_3)_3C-$ | H | —⟨phenyl, Cl⟩—$CF_3$ | H | 90-91 |
| 17 | $(CH_3)_3C-$ | H | —⟨phenyl, Cl⟩—$S-CF_2Cl$ | H | 118-119 |
| 18 | $(CH_3)_3C-$ | H | —⟨phenyl⟩—O—⟨phenyl⟩—Cl | F | 82-85 |
| 19 | $(CH_3)_3C-$ | H | $-CH_2-CH=CH_2$ | F | viscous oil |
| 20 | $(CH_3)_3C-$ | $CH_3$ | $-CO-CH_3$ | F | 100/0,5mm |
| 21 | $(CH_3)_3C-$ | $CH_3$ | $-SCCl_3$ | F | 44-47 |
| 22 | $(CH_3)_3C-$ | $CH_3$ | —S-dimer | F | 103-106 |
| 23 | $(CH_3)_2CH-$ | H | $CH_3$ | H | $n_D^{22}=1,4583$ |
| 24 | $(CH_3)_3C-$ | $CH_3$ | $-S-CCl_2F$ | F | viscous oil |

It will be appreciated that the instant specification and examples are set forth by way of illustration and not limitation, and that various modifications and changes may be made without departing from the spirit and scope of the present invention.

What is claimed is:

1. An oxime-carbamate of a fluorinated ketone of the formula

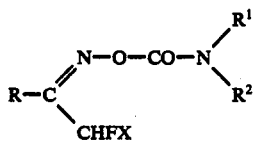

in which

X is hydrogen or fluorine.

R is alkyl with 1 to 6 carbon atoms optionally substituted by halogen, nitro, cyano, hydroxyl, —S-$C_{1-4}$-alkyl, —O-$C_{1-4}$-alkyl, —CO-O-$C_{1-4}$alkyl or —O-CO-$C_{1-4}$-alkyl;

or phenyl optionally substituted by halogen, alkyl with 1 to 4 carbon atoms or halogenoalkyl with 1 or 2 carbon atoms and up to 5 halogen atoms; phenylalkyl with 1 to 4 carbon atoms in the alkyl moiety and optionally substituted in the phenyl moiety by halogen, alkyl with 1 to 4 carbon atoms or halogenoalkyl with 1 to 2 carbon atoms and up to 5 halogen atoms; or cycloalkyl with 5 to 7 carbon atoms optionally substituted by halogen, alkyl with 1 to 4 carbon atoms or halogenoalkyl with 1 or 2 carbon atoms and up to 5 halogen atoms;

R¹ is hydrogen, alkyl with 1 to 12 carbon atoms, alkenyl or alkynyl each with 2 to 4 carbon atoms, halogenoalkyl with up to 2 carbon atoms and up to 5 halogen atoms, halogenoalkenyl with up to 3 carbon atoms and up to 5 halogen atoms, alkoxyalkyl or alkythioalkyl with up to 2 carbon atoms in each alkyl moiety, or phenyl optionally substituted by halogen, alkyl with 1 to 4 carbon atoms, halogenoalkyl, halogenoalkoxy or halogenoalkylthio each with 1 to 2 carbon atoms and up to 5 halogen atoms, $C_{1-2}$-alkoxy, $C_{1-2}$-alkylthio phenyl, phenoxy, halophenyl, halophenoxy, nitro or cyano;

R² is any of R¹ or —SR³,

R³ is alkyl with 1 to 4 carbon atoms, halogenoalkyl with 1 to 2 carbon atoms and up to 5 halogen atoms, phenyl optionally substituted by halogen, alkyl with 1 or 2 carbon atoms or halogenoalkyl with 1 to 2 carbon atoms and up to 5 halogen atoms; alkoxycarbonyl with 1 to 4 carbon atoms in the alkoxy moiety; a radical identical to that to which the —SR³ is bonded; or —NR⁴-$SO_2$-R⁵;

R⁴ is alkyl with 1 to 4 carbon atoms;

R⁵ is alkyl with 1 to 5 carbon atoms; dialkylamino with 1 to 4 carbon atoms in each alkyl moiety; or phenyl optionally substituted by halogen, alkyl with 1 to 2 carbon atoms, halogenoalkyl with 1 to 2 carbon atoms and up to 5 halogen atoms, cyano or nitro, or an acid addition salt.

2. The compound according to claim 1, wherein such compound is 1,1-difluoro-3,3-dimethyl-2-methylcarbamoyl-oximino-butane of the formula

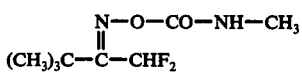

or an acid addition salt thereof.

3. The compound according to claim 1, wherein such compound is 1,1-difluoro-3,3-dimethyl-2-[N-methyl-N-(3-trifluoromethylphenylmercapto)]-carbamoyl-oximino-butane of the formula

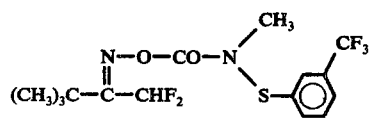

or an acid addition salt thereof.

4. The compound according to claim 1, wherein such compound is 1,1-difluoro-3,3-dimethyl-2-(N-methyl-N-trichloromethylmercapto)-carbamoyl-oximino-butane of the formula

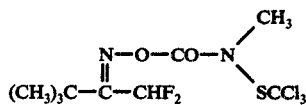

or an acid addition salt thereof.

5. The compound according to claim 1, wherein such compound is 1-fluoro-3-methyl-2-methylcarbamoyl-oximino-butane of the formula

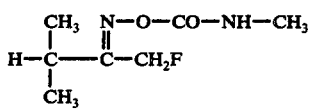

or an acid addition salt thereof.

6. The compound according to claim 1, wherein such compound is 1-fluoro-3,3-dimethyl-2-(N-methyl-N-dichlorofluoromethylmercapto)carbamoyl-oximino-butane of the formula

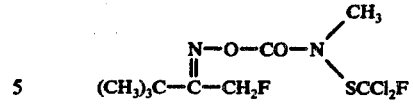

or an acid addition salt thereof.

7. An arthropodicidal or nematicidal composition containing as active ingredient an arthropodicidally or nematicidally effective amount of a compound according to claim 1 in admixture with a diluent.

8. A method of combating arthropods or nematodes which comprises applying to the arthropods or nematodes or to a habitat thereof, an arthropodicidally or nematicidally effective amount of a compound according to claim 1.

9. The method according to claim 8 wherein such compound is 1,1-difluoro-3,3-dimethyl-2-methylcarbamoyl-oximino-butane, 1,1-difluoro-3,3-dimethyl-2-[N-methyl-N-(3-trifluoromethylphenylmercapto)]-carbamoyl-oximino-butane, 1,1-difluoro-3,3-dimethyl-2-(N-methyl-N-trichloromethylmercapto)-carbamoyl-oximino-butane, 1-fluoro-3-methyl-2-methylcarbamoyl-oximino-butane, or 1-fluoro-3,3-dimethyl-2-(N-methyl-N-dichlorofluoromethylmercapto)-carbamoyl-oximino-butane or an acid addition salt thereof.

* * * * *